United States Patent [19]

Schuierer et al.

[11] 4,209,407
[45] Jun. 24, 1980

[54] FIRE EXTINGUISHING AGENT

[75] Inventors: Erich Schuierer, Burghausen; Heinrich Bathelt, Altötting; Richard Bröll, Langen, all of Fed. Rep. of Germany

[73] Assignee: Hoechst Aktiengesellschaft, Frankfurt am Main, Fed. Rep. of Germany

[21] Appl. No.: 890,203

[22] Filed: Mar. 27, 1978

[30] Foreign Application Priority Data

Mar. 30, 1977 [DE] Fed. Rep. of Germany ....... 2714013

[51] Int. Cl.² .......................... A62D 1/00; A62C 1/12
[52] U.S. Cl. .......................................... 252/3; 169/47; 252/8.05
[58] Field of Search ...................... 252/3, 8.05; 169/47

[56] References Cited

U.S. PATENT DOCUMENTS 3,856,535  12/1974  Ferguson ............................. 252/8.1
4,099,574  7/1978   Cooper et al. ........................... 252/3

Primary Examiner—Leland A. Sebastian
Attorney, Agent, or Firm—Connolly and Hutz

[57] ABSTRACT

New aqueous concentrates containing a fluorinated surfactant and a further foam producing component are disclosed. They contain of from 0.5 to 2.5% by weight a fluorinated phosphorous acid ester having the formula

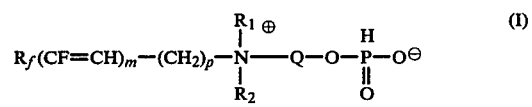

In this formula means $R_f$ a perfluoroalkyl radical with from 3 to 16 carbon atoms, m zero or 1, p an integer of from 1 to 4, $R_1$ a hydrogen atom, a $C_{1-4}$ alkyl radical, a cylcohexyl radical or a 2-hydroxyalkyl radical with from 2 to 6 carbon atoms, $R_2$ a $C_{1-4}$ alkyl radical, a cyclohexyl radical or a 2-hydroxyalkyl radical with 2 to 6 carbon atoms, or a radical of the formula $R_f$—$(CF=CH)_m$—$(CH_2)_p$, Q an alkylene radical with 2 to 4 carbon atoms, which may be substituted by phenyl groups. The aqueous concentrate when diluted with about 16 parts by volume of water gives a solution which can be foamed. The foam it capable of extinguishing liquid hydrocarbon fires.

15 Claims, No Drawings

FIRE EXTINGUISHING AGENT

The present invention relates to fire extinguishing agents, which contain as the main constituent a surface-active fluorine compound. Surface-active fluorine compounds have been used in recent years in fire protection. Their particular importance resides in the fact that they disperse on non-polar combustible liquids in the presence of water to form an aqueous film which covers the whole surface and, to a certain degree, provides a protection against reignition.

It has been ascertained that frequently a concentration of a fluorinated surfactant of about 0.1% by weight, calculated on the aqueous solution to be foamed, suffices to extinguish hydrocarbon fires and that the surface tension of this solution should be below 20 dyn/cm, if possible.

Fluorinated surfactants are relatively expensive. It was, consequently, a task to develop a cheap fluorinated surfactant which fulfills the above requirements when used in practice.

It has now been found that phosphorous acid esters of the formula

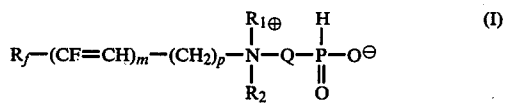

are excellently suitable as a constituent of foam fire extinguishing agents. In the above formula $R_f$ is a perfluoroalkyl radical with from 3 to 16 carbon atoms, m is 0 or 1, p is an integer of from 1 to 4, $R_1$ is a hydrogen atom, a $C_{1-4}$ alkyl radical, a cyclohexyl radical or a 2-hydroxyalkyl radical with from 2 to 6 carbon atoms, $R_2$ is a $C_{1-4}$ alkyl radical, a cyclohexyl radical, a 2-hydroxyalkyl radical with from 2 to 6 carbon atoms, or a radical of the formula $R_f-(CF=CH)_m-(CH_2)_p-$, Q is an alkylene radical with from 2 to 4 carbon atoms, which may be substituted by phenyl groups.

This is applicable, for example to foam extinguishing agents, in which the foam producing component is protein hydrolysate or a synthetic imputrescible organic surfactant. In both cases, additions of the fluorine component I in small amounts improve the extinction effect. Advantageously component I is employed together with a second foam producing fluorinated surfactant component. Among appropriate second components, cation active surfactants may be mentioned, especially, however, non ionic surfactants containing a perfluoroalkyl group.

Excellently suitable are in particular non ionic fluorine-containing amides of the formula II $$F(CF_2)_a.CONH(CH_2)_3N(CH_2CH_2OH)_2 \qquad (II),$$

in which a is an integer of from 6 to 10.

Fluorine-containing amides of this type are known from German Auslegeschrift No. 21 27 232.

The present foam concentrates have the advantage that a fluorinated surfactant II which considerably reduces the surface tension is combined with a fluorinated surfactant I which has a rather high surface tension but which can be obtained in cheap manner. Thus, there is obtained a cheap and appropriate water film-forming foaming agent.

Suitable compounds of the formula I are especially compounds of the formula Ia

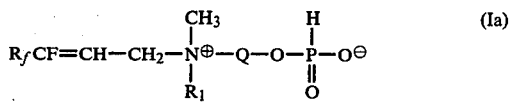

in which $R_1$ is an alkyl radical with from 1 to 4 carbon atoms, a 2-hydroxyalkyl radical with from 1 to 4 carbon atoms or a hydrogen atom.

Especially preferred are compounds of the formula Ib

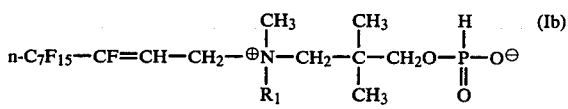

It has moreover been found that, instead of the phosphorus-containing esters I compounds of the formula III free from phosphorus

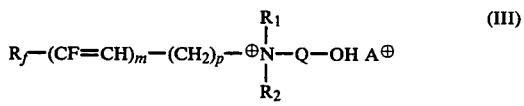

in which $R_f$, m, p, $R_1$, $R_2$ and Q are defined as in formula I and $A^\ominus$ is a water-solubilizing anion, may be used together with the compounds of the formula II as additives to foam-type fire-fighting agents.

The anion $A^\ominus$ is not critical. For example anions such as nitrate, sulfate, acetate or halide, especially methosulfate, may alternatively be used.

Especially suitable for this purpose are those representatives of the formula III which have the formula

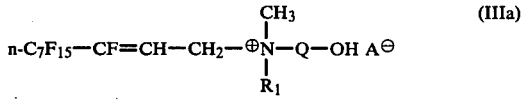

In the formula III Q and $A^\ominus$ have the same meaning as in the formula III, $R_1$ is an alkyl radical with from 1 to 4 carbon atoms, preferably 1 to 2 carbon atoms, especially the methyl radical. Suitable anions $A^\ominus$ are for example halides, for example a bromide or iodine, or methosulfate or an acetate.

The weight ratio between II and III or between II and IIIa is at most 1, but is preferably in the range of from 0.5 to 0.05, in particular of from 0.3 to 0.1. The absolute quantity of fluorinated surfactant in the foam concentrate (prior to adding the extinguishing water) is in the range of from about 0.5 to 2.5, preferably of from 1 to 2% by weight. These relations may also be applied to the system II/I.

Suitably the radical $R_f$ in the compounds I and III has of from 5 to 12 carbon atoms. Advantageously Q is —$C_2H_4$— or

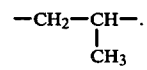

Preferably the product (m·p) is zero or 1.

The foam concentrate may contain, in addition to fluorinated surfactants, water and the foam-producing component (synthetic surfactant or protein hydrolysate) further known additives, for example antifreezing agents, corrosion inhibitors and foam improving agents. Suitable foam-improving agents are, for example, alkyl glycols such as monoalkylethyllene glycol having $C_{1-4}$ aklyl. The portion of these alkylglycols in the foam concentrate may amount up to 35% by weight and is preferably in the range of from 20 to 30% by weight.

For extinguishing purposes, the foam concentrate is diluted with water and thereafter foamed. The dilution is effected with water for example in a 10- to 20-fold quantity of the foam concentrate. The solution entering the foam tube, consequently, contains of from about 91 to 97% by weight of water. The solution also contains from 0.01 to 1%, especially 0.03 to 0.3% of the fluorinated surfactant of formula I.

The foam production may be carried out in usual manner, by injecting air (or an other noncombustible gas). The compounds of the formula II are known, for example from U.S. Pat. Nos. 3,257,407; 3,535,381; German Offenlegungsschriften 22 44 297; 21 41 542 and 17 68 939 and may thus be prepared according to known processes.

Especially suitable for the admixture with compounds of the formula II are those compounds of the formula III in which at least one of the radicals $R_1$ and $R_2$ is a 2-hydroxyalkyl radical having of from 1 to 4 carbon atoms. The compounds of the formula I may be obtained from amines of the formula

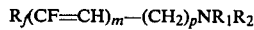
$$R_f(CF=CH)_m-(CH_2)_pNR_1R_2$$

by reaction with cyclic phosphites of the formula

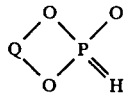

at a temperature of from +20° to +140° C. The reaction is preferably carried out in the presence of polar solvents.

Said reaction is preferably carried out at a temperature of from +20° to +140° C., preferably of from +60° to +140° C., suitably while first placing the fluorine-containing amine heated to the reaction temperature into the reaction vessel and slowly adding the cyclic phosphorous acid ester serving as the alkylation agent until equimolar weight ratio habe been set up. Furthermore it is advisable to superpose the reaction mixture with an inert gas, for example nitrogen. The reaction is preferably carried out at atmospheric pressure, but may likewise be performed under reduced pressure, or especially suitably in the presence of solvents, under a slightly elevated pressure. The reaction requires on principle no solvent.

However, for a better handling of the starting and final products, which are highly viscous at room temperature, polar solvents are suitably used which advantageously should be capable of dissolving both the starting and the final products. Especially appropriate are polar solvents, for example methanol, ethanol, isopropanol, methylene chloride, chloroform, glycol and dimethylglycol. At the generally employed reaction temperatures of from +60° to +120° C., the reaction ends after about 2 to 4 hours. However, it has proved advantageous to add during the reaction process a small quantity of water, preferably of from 1 to 10 mol %, in order to improve the conversion and the reaction velocity.

Further details concerning the preparation of the phosphorous acid esters I may be found in copending application Ser. No. 859,051 filed Dec. 9, 1977, now U.S. Pat. No. 4,147,743. The invention will be illustrated by the following examples:

EXAMPLES

The tests were on principle carried out using the following standard test method:

A circular fire basin (diameter 1.9 m; area of fire 2.83 m²; height of the basin 20 cm) was filled each time with 150 liters of jet propellant JP 4. After the propellant had been set on fire and burned for a period of 2 minutes, the aqueous foamable solution containing the fluorinated surfactant with a content of foam concentrate of 6% by volume was directly sprayed on to the fire by means of a laborator-type foam jet tube, at a rate of 10 liters/minute of water flow, at an angle of inclination of 45° C. The foaming number (ratio between volume of the foam and volume of the used liquid) was about 7 to 8. The following foam concentrates were examined and the extinction time was determined:

EXAMPLE 1

0.2% by weight of fluorine-containing surfactant
$C_7F_{15}CONH(CH_2)_3N(CH_2CH_2OH)_2$ 1.3% by weight of fluorine-containing surfactant $$C_7F_{15}CF=CH-CH_2-\overset{\oplus}{\underset{\underset{CH_3}{|}}{N}}-CH_2-\underset{\underset{CH_3}{|}}{\overset{\overset{C_2H_4OH}{|}}{C}}-CH_2-O\overset{\overset{H}{|}}{\underset{\underset{O}{\|}}{P}}-O^{\ominus}$$

10.0% by weight of $C_{12-16}$ alkylsulfate as effective foaming agent, triethanol amine salt,
25.0% by weight of ethylene glycol as antifreezing agent
25.0% by weight of butyl glycol as antifreezing agent
38.5% by weight of water
100.0% by weight of foaming concentrate
extinction time: 60 seconds.

EXAMPLE 2

0.2% by weight of fluorine-containing surfactant
$C_7F_{15}CONH(CH_2)_3N(CH_2CH_2OH)_2$
1.3% by weight of fluorine-containing surfactant
$(C_7F_{15}CF=CH-CH_2-\overset{\oplus}{N}(CH_3)_2C_2H_4OH)SO_4CH_3^{\ominus})$
10.0% by weight of alkylsulfate of Example 1
25.0% by weight of butylglycol as antifreezing agent
25.0% by weight of ethylene glycol as antifreezing agent
38.5% by weight of water
100.0% by weight of foam concentrate
extinction time: 60 seconds

EXAMPLE 3

0.2% by weight of fluorine-containing surfactant
$C_7F_{15}CONH(CH_2)_3N(CH_2CH_2OH)_2$
1.3% by weight of fluorine-containing surfactant
$(C_7F_{15}CF=CH-CH_2-\overset{\oplus}{N}(CH_3)_2C_2H_4OH)$ $Cl^{\ominus}$
10.0% by weight of alkylsulfate of Example 1
25.0% by weight of butylglycol as antifreezing agent
25.0% by weight of ethylene glycol as antifreezing agent
38.5% by weight of water
100.0% by weight of foam concentrate -continued extinction time: 50 seconds

EXAMPLE 4

| |
|---|
| 1.5% by weight of the phosphorus-containing fluorinated surfactant of Example 1 |
| 10.0% by weight of alkylsulfate of Example 1 |
| 25.0% by weight of butylglycol as antifreezing agent |
| 25.0% by weight of ethylene glycol as antifreezing agent |
| 38.5% by weight of water |
| 100.0% by weight of foam concentrate |
| extinction time: after 90 seconds, control of the fire, but no complete extinction. |

EXAMPLE 5

Example 4 was repeated under modified test conditions. There was used a circular concrete fire basin of a surface of 10 m² in which the height of the water was 5 cm. The nature and the quantity of the combustion substances corresponded to those of Example 1. The oil layer in the trough was about 3 cm thick.

period of burn: 15 seconds
foam jet tube: 25 liter/min. of water flow, direct application of the foam.
Additive: 5% by volume to the extinction water.
Average extinction time: 3 minutes, 44 seconds.

EXAMPLE 6

The foam concentrate of Example 1 was examined under the conditions of Example 5.

Average extinction time: 2 minutes, 24 seconds.

EXAMPLE 7

The following composition was tested under the conditions of Example 1:

| |
|---|
| 1.5% by weight of fluorinated surfactant $C_7F_{15}CONH(CH_2)_3N(CH_2CH_2OH)_2$ |
| 10.0% by weight of alkylsulfate of Example 1 |
| 25.0% by weight of butylglycol as antifreezing agent |
| 25.0% by weight of ethylene glycol as antifreezing agent |
| 38.5% by weight of water |
| 100.0% by weight of foam concentrate |
| extinction time: of from 50 to 60 seconds. |

EXAMPLE 8

Into a glass flask equipped with stirrer, reflux condenser, dropping funnel and thermometer were placed 399.2 g (1.0 mol) of $C_5F_{11}CF=CH-CH_2-N(C_2H_5)_2$, 500 ml of isopropanol and 5 ml of water, the batch was heated to the boiling point of isopropanol and thereafter 150.1 g (1.0 mol) of a cyclic phosphite of the formula

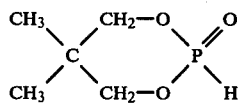

were added during 20 minutes. The reaction mixture was further refluxed for 4 hours. Upon completion of the reaction, isopropanol was distilled off and small quantities of the solvent were removed by applying a water pump vacuum. A light-brown oil was obtained which was highly viscous at room temperature and well soluble in water.

Yield of phosphorous acid ester: 545.6 g, which corresponded to

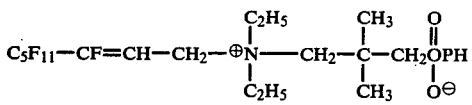

What is claimed is:

1. Foam concentrate for fire-fighting purposes which contains water, at least one foam producing fluorinated surfactant and a further foam producing component, and which has a content of from 0.5 to 2.5% by weight of a fluorinated phosphorous acid ester of the formula

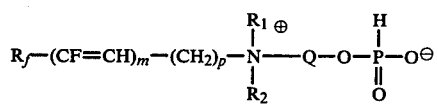

in which
$R_f$ is a perfluoroalkyl radical with from 3 to 16 carbon atoms,
m is zero or 1,
p is an integer of from 1 to 4,
$R_1$ is a hydrogen atom, a $C_{1-4}$ alkyl radical, a cyclohexyl radical or a 2-hydroxyalkyl radical with from 2 to 6 carbon atoms,
$R_2$ is a $C_{1-4}$ alkyl radical, a cyclohexyl radical or a 2-hydroxyalkyl radical with 2 to 6 carbon atoms, or a radical of the formula $R_f-(CF=CH)_m-(CH_2)_p$, and
Q is an alkylene radical with 2 to 4 carbon atoms which may be substituted by phenyl groups, or the radical $-CH_2-C(CH_3)_2-CH_2-$.

2. Foam concentrate as claimed in claim 1, which has a content of said ester of from 1 to 2% by weight.

3. Foam-type fire extinguishing concentrate as claimed in claim 1, which contains as a further foam component a hydrocarbon surfactant.

4. Foam concentrate as claimed in claim 1, which contains as a further foam producing component a protein hydrolysate.

5. Foam concentrate as claimed in claim 1, which contains as a further foam producing component a non ionic fluorinated surfactant.

6. Foam concentrate as claimed in claim 5, wherein the non-ionic fluorinated surfactant has the formula $$F(CF_2)_a-CONH(CH_2)_3N(CH_2CH_2OH)_2$$

in which a is an integer of from 6 to 10.

7. Foam concentrate as claimed in claim 5, wherein the weight ratio non-ionic fluorinated surfactant/fluorine-containing phosphorous acid ester is smaller than 1 or equal to 1.

8. Foam concentrate as claimed in claim 7, wherein the weight ratio non-ionic fluorinated surfactant/fluorine-containing phosphorous acid ester is in the range of from 0.5 to 0.05.

9. Foam concentrate as claimed in claim 1, wherein a phosphorous acid ester of the formula

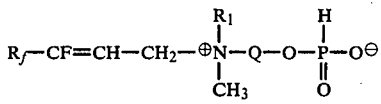

is used in which
- $R_f$ is a perfluoroalkyl radical with from 3 to 16 carbon atoms,
- $R_1$ is a hydrogen atom, a $C_{1-4}$ alkyl radical, a cyclohexyl radical or a 2-hydroxyalkyl radical with from 2 to 6 carbon atoms, and
- Q is an alkylene radical with 2 to 4 carbon atoms which may be substituted by phenyl groups, or the radical $-CH_2-C(CH_3)_2-CH_2-$.

10. Foam concentrate as claimed in claim 9, wherein a phosphorous acid ester of the formula

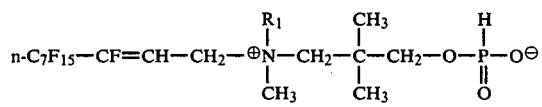

is used.

11. Foam concentrate as claimed in claim 1, containing from 0 up to 35% by weight of a monoalkyl ethylene glycol.

12. Process for the extinction of a burning liquid hydrocarbon by covering the area of fire with a foam consisting of a non combustible gaseous phase and an aqueous liquid phase, wherein the liquid phase contains of from 0.01 to 1% by weight of an ester of claim 1.

13. Process as claimed in claim 12, wherein the content of said ester is in the range of from 0.03 to 0.3% by weight.

14. Foam concentrate for fire-fighting purposes, containing water, at least one foam producing fluorinated surfactant and a further foam producing component which comprises an ionic fluorine-containing compound of the formula

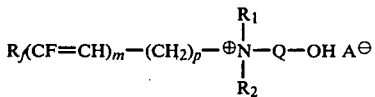

in which
- $R_f$ is a perfluoroalkyl radical with from 3 to 16 carbon atoms,
- m is zero or 1,
- p is an integer of from 1 to 4,
- $R_1$ is a hydrogen atom, a $C_{1-4}$ alkyl radical, a cyclohexyl radical or a 2-hydroxyalkyl radical with from 2 to 6 carbom atoms,
- $R_2$ is a $C_{1-4}$ aklyl radical, a cyclohexyl radical or a 2-hydroxyalkyl radical with 2 to 6 carbon atoms, or a radical of the formula $R_f-(CF=CH)_m-(CH_2)_p$,
- Q is an alkylene radical with 2 to 4 carbon atoms which may be substituted by phenyl groups, or the radical $-CH_2-C(CH_3)_2-CH_2-$, and
- $A^\ominus$ is a water-solubilizing anion, and non-ionic fluorinated compound of the formula
$F(CF_2)_a \cdot CONH(CH_2)_3N(CH_2CH_2OH)_2$ in which a is an integer of from 6 to 10.

15. Concentrate as claimed in claim 14, wherein the weight ratio of non-ionic fluorinated compound to ionic fluorine-containing compound is smaller than 1 or equal to 1 and the absolute quantity of fluorinated surfactant is in the range of from 0.5 to 2.5% by weight.

* * * * *